(12) United States Patent
Flesch et al.

(10) Patent No.: US 7,798,971 B2
(45) Date of Patent: Sep. 21, 2010

(54) MOTORIZED ULTRASONIC SCANHEAD (75) Inventors: Aimé Flesch, Andrésy (FR); An Nguyen-Dinh, Valleres (FR)

(73) Assignee: Vermon, Tours (FR)

( * ) Notice: Subject to any disclaimer, the term of this patent is extended or adjusted under 35 U.S.C. 154(b) by 730 days.

(21) Appl. No.: 11/175,138

(22) Filed: Jul. 7, 2005

(65) Prior Publication Data

US 2007/0038110 A1  Feb. 15, 2007

(51) Int. Cl.
*A61B 8/14* (2006.01)
(52) U.S. Cl. .................. 600/459; 600/437; 600/407; 340/573.1; 367/87
(58) Field of Classification Search .......... 600/407–408
See application file for complete search history.

(56) References Cited

U.S. PATENT DOCUMENTS

| | | | |
|---|---|---|---|
| 4,374,525 A | | 2/1983 | Baba |
| 4,375,818 A | | 3/1983 | Suwaki et al. |
| 5,085,221 A | | 2/1992 | Ingebrigtsen et al. |
| 5,176,141 A | | 1/1993 | Bom et al. |
| 5,181,514 A | * | 1/1993 | Solomon et al. ............ 600/444 |
| 5,413,107 A | | 5/1995 | Oakley et al. |
| 5,445,154 A | * | 8/1995 | Larson et al. ............... 600/459 |
| 5,681,263 A | | 10/1997 | Flesch |
| 6,019,726 A | | 2/2000 | Webb |
| 6,171,248 B1 | * | 1/2001 | Hossack et al. ............. 600/459 |
| 7,066,889 B2 | * | 6/2006 | Taylor ....................... 600/459 |
| 7,077,808 B2 | * | 7/2006 | Couvillon, Jr. .............. 600/466 |
| 2002/0188200 A1 | * | 12/2002 | Mauchamp et al. ......... 600/439 |
| 2002/0188201 A1 | * | 12/2002 | Crowley ..................... 600/439 |
| 2003/0229287 A1 | * | 12/2003 | Flesch et al. ................ 600/466 |
| 2006/0253028 A1 | * | 11/2006 | Lam et al. ................... 600/459 |

* cited by examiner

*Primary Examiner*—Brian Casler
*Assistant Examiner*—Nasir Shahrestani
(74) *Attorney, Agent, or Firm*—Stites & Harbison PLLC; Ross F. Hunt, Jr.; Jeffrey A. Haeberlin (57) ABSTRACT

A motorized scanhead device is capable of rotating an array transducer through 360 degrees of angular rotation in a manner such as to provide acquisition of images in successive scanning planes arranged around the principal axis of the device. The device can be incorporated in endoscopes (e.g., transesophageal endoscopes), laparoscopes, endocavity or intracavity probes so as to provide an expanded angle of vision or to render 3D images, without the need for external movement of the device. The motorized scanhead device includes a motor that is isolated from the transducer signal interconnections in order to minimize electrical discharges associated with motor operation and to provide more room between an associated probe housing and the scanhead device.

15 Claims, 5 Drawing Sheets

MOTORIZED ULTRASONIC SCANHEAD

FIELD OF THE INVENTION

This invention relates to ultrasonic diagnostic scanheads and, more particularly, to a motorized scanhead device capable of rotating an array transducer through 360 degrees of rotation to provide image acquisition.

DESCRIPTION OF THE RELATED ART

Ultrasonic imaging apparatus dedicated to endocavity or intracavity operations are well known especially in diagnostic applications such as celioscopy, TE Transesophageal Echography, laparoscopy, and transvaginal and transrectal applications. In addition, probes for intraluminal or intravascular use are very similar except for their smaller diameter. All of these apparatus has a common characteristic, viz., an ultrasonic scanhead is assembled at the distal tip of the probe so as to allow imaging of regions of the tissue being examined which are located remotely and cannot be directly accessed.

With respect to the endocavity modalities currently being practiced, the existing apparatus are typically provided with either a fixed array transducer or a dual transducer or a moving array transducer for multiplane or volume rendering operations. In many cases, the array transducer is mounted longitudinally with respect to the probe axis and can, therefore, provide scanning of a lateral scanning plane to provide a sector scan. In some circumstances, it is desirable for the transducer to be able to rotate around its longitudinal axis so as to acquire multiplane information or to track a target (e.g., cysts or a biopsy needle). Currently, this action can be carried out by either rotating the probe or the transducer. However, such rotation of the probe may cause significant discomfort to the patient and present risks during manipulation.

Imaging apparatus having a transducer tip capable of rotation with reference to the probe handle have been disclosed, for example, in U.S. Pat. No. 5,413,107 to Oakley and U.S. Pat. No. 5,681,263 to Flesch. An articulated ultrasonic probe for endoscopic examination having rotation means for the articulated section of the probe is disclosed in the Oakley patent. In this patent, an array transducer is mounted at the distal tip of the endoscope tube. The distal portion can be steered in four different directions by actions manually exerted on control cables through commands provided at the handle of the probe. The transducer head is enabled to rotate by the use of a bellows attached to a rigid tube through which the movement is transmitted. The use of the rigid tube in combination with the bellows allows the apparatus to be rotated even in an articulated position. However, as long as the rigid tube provides sheathing externally if the endoscope, any movement of the transducer will be directly communicated to the external medium and this can lead to patient discomfort and a risk of wounding or other damage to the organ in contact with the probe. Further, sealing problems and problems with disinfection of the instrument may also occur with the use of seals.

An improvement in the probe of the Oakley patent is disclosed in the Flesch patent wherein the transducer tip is made to rotate internally by cable control. Neither a transmission tube nor a bellows is therefore required. The movement of the transducer only affects the articulated portion of the probe apparatus, thus decreasing patient discomfort and the risk of injury to the tissue.

However, the devices of both patents discussed above still suffer drawbacks and disadvantages. The latter include, for example, the interdependence between the articulation mechanism and the rotation of the transducer (and the corresponding variation of resistance torsion stiffness versus the angle of articulation), the inaccuracy induced by movement of the transducer combined with the effect of friction, and the lack of compatibility with precision 3D acquisition or real time volume image rendering.

Endoscope probes providing rotating of the transducer mounted inside of the probe are disclosed in U.S. Pat. No. 4,374,525 to Baba. In this patent, an ultrasonic diagnostic apparatus for an endoscope includes a bendable insertable section of the endoscope that is equipped with an ultrasonic transducer at the distal tip. The tip comprises a liquid bath in which is immersed a rotating transducer unit. The transducer unit is assembled to a drive shaft having a hollow space for passing the transducer interconnections to the handle. Because the shaft and the transducer are rotated, slip ring devices are used for transmitting the electrical signals from the moving shaft to the external electrical connectors for the probe. Articulation of the transducer tip is provided by hinges disposed behind the transducer assembly. It is therefore apparent that this approach cannot be practically applied to devices that include an array transducer wherein hundreds of transducer interconnections are required.

An arrangement which avoids positioning of the moving member between the transducer and the handle of the probe is disclosed in U.S. Pat. No. 4,375,818 to Suwaki. This patent discloses an ultrasonic diagnostic apparatus associated with an optical system for the examination of the coeliac cavity. In one embodiment, an alternative form of the apparatus is provided wherein a motorization or drive means, e.g., a motor, is housed within the foremost portion of the distal tip. A driving mechanism is disposed between the transducer and the motor. The transducer is immersed in a liquid bath and gaskets are used for preventing leakage of liquid. In this patent, providing transducer interconnections does not present a problem, and a passageway forl cables for the motor power supply is provided underneath a chamber containing the transducer. However, this approach still has a number of shortcomings that prevent complete rotation of the transducer. These include the presence of the electrical connections for the motor. Further, there is a risk of liquid leakage through the motor shaft and this makes such an apparatus unreliable for use in continuous operation (as is required in 3D rendering operations).

An arrangement wherein an array transducer is rotated with reference to its longitudinal axis is disclosed in U.S. Pat. No. 5,085,221 to Ingebrigtsen. This patent discloses a TE transducer head comprising a cylindrical housing, an end cap, a motor coupled to an array transducer to provide rotation thereof, a position sensor axially aligned with the motor, and a set of flexible cables for providing electrical connections to the array transducer. Although his patent does not disclose the coupling mode between the array transducer and the end cap, it can be assumed that an internal space within the housing is filled with coupling liquid for the transmission of acoustic energy to the medium. The transducer head can also be plugged to an endoscope or probe housing using an interconnection interface provided at the proximal end of the device. As provided in a preferred embodiment, the back side or rear of the array transducer is connected to a first flexible cable that is, in turn, connected to a second flat cable or conductor adaptor. Direct drive of the transducer provided by the motorization means (e.g., motor) and controlled by the position sensor enables the apparatus to be compatible with 3D acquisition or with real time volume rendering. However, the approach disclosed in this patent suffers at least two major limitations. First, the transducer cannot perform a complete rotation (because of the interconnection cables). Second, the rotation velocity of the transducer will be significantly slowed by the liquid resistance of the coupling liquid used in this type of transducer.

In U.S. Pat. No. 5,176,141 to Bom, a disposable catheter probe is disclosed for intraluminal applications. In one preferred embodiment, a motor or motorization means is disposed at the distal portion (tip end) of the apparatus, and provides rotation of an acoustic mirror that laterally steers the ultrasonic energy issued from a transducer arranged along the longitudinal axis of the probe. No movement of the transducer is required to obtain a cylindrical scanning image and, in general, the rotational speed of the acoustic mirror can be set to be as high as desired. On the other hand, rotation of the acoustic mirror as described in the patent requires the use of a liquid chamber for acoustically coupling the ultrasonic energy. This results in a need for dynamic seals for protection of the motor, and such seals often exhibit a lack of reliability and durability. Another shortcoming of this approach concerns the positioning of the transducer. This positioning does not permit the assembly of linear arrays due to the lack of room in the lateral dimension. Thus, this approach is not suitable for use in volume acquisition modalities.

Others endoscopes and intravascular ultrasound (IVUS) devices provide for rotating the transducer by use of a driveshaft driven by a remotely located motorization means (e.g., a motor located in the handle of the probe). This method results in non-uniform angular velocity so that the rotational speed must be corrected by a position sensor co-located with the transducer as well as dedicated servo-control electronics to ensure precise positioning of the transducer when rotated. For example U.S. Pat. No. 6,019,726 to Webb discloses a method for correcting the non-uniform velocity of a transducer.

Given the state of the art of ultrasonic endoscopic/intraluminal probes as described above, there is obviously a-need for an ultrasonic scanhead dedicated to such a probe which is capable of providing transducer rotation through angles of up to 360 degrees.

SUMMARY OF THE INVENTION

One object of the invention is to provide a probe providing transducer rotation through angles up to 360 degrees using an arrangement wherein linear arrays are mounted in axial alignment with the probe body without a rotation or drive means mounted between the transducer and the probe handle.

It is a further object of the present invention to provide an ultrasonic endoscope/intraluminal probe wherein a motorization means is assembled at an end portion of the probe and wherein a complete cylindrical scanning operation can be performed using a linear array transducer mounted parallel to a lateral surface of the endoscope/intraluminal probe body.

It is still another object of the present invention to provide a rotating linear array scanhead having improved EMI protection for transducer signals supplied to the external cables.

It is still a further object of the present invention to provide an ultrasonic scanhead for endoscope/intraluminal probes wherein rotating linear arrays are electrically connected to winding flexible circuits in such a manner as to allow rotation through at least 360 degrees, without any resultant movement of the output portion of the flexible circuits.

According to one aspect of the invention, there is provided a motorized ultrasonic scanhead device which is capable of providing rotation of an associated array transducer through an angle of 360° or more, so as to enable image acquisition for successive scanning planes being arranged around the principal axis of the device. The device of the invention can be implemented as part of, i.e., can be incorporated in, endoscopes (e.g., transesophageal endoscopes), laparoscopes, endocavity or intracavity probes so as to provide an expanded angle of vision or to render 3D images without the need for external movement of the device. A further aspect of this invention concerns a motorized scanhead wherein the motorization means or motor is isolated from transducer signal interconnections in order to minimize any electrical discharges associated with motor operations and to also provide more room for the assembly between the probe housing and the scanhead device.

It will be understood that different aspects of the present invention that are disclosed with respect to the principles of the invention can be extended to any type of imaging apparatus having an elongated member or tube terminating in a scanning tip, including endoscopes, intraluminal catheters, endocavity probes and the like.

Further features and advantages of the present invention will be set forth in, or apparent from, the detailed description of preferred embodiments thereof which follows.

BRIEF DESCRIPTION OF THE DRAWINGS

FIG. 9(b) is a transverse cross-sectional view of the scanhead of FIG. 9a;

DESCRIPTION OF THE PREFERRED EMBODIMENTS

Figure 1A:
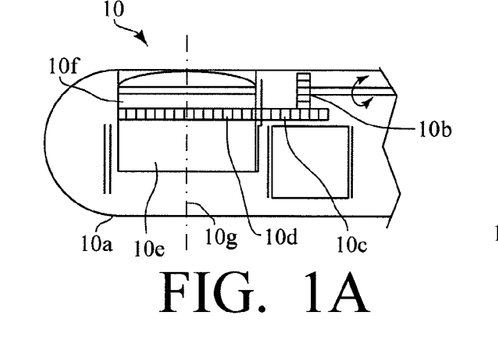
FIGS. 1(a), 1(b) and 1(c) are schematic longitudinal cross-sectional views of respective prior art probes providing different modes of transducer movement.
Figure 1B:
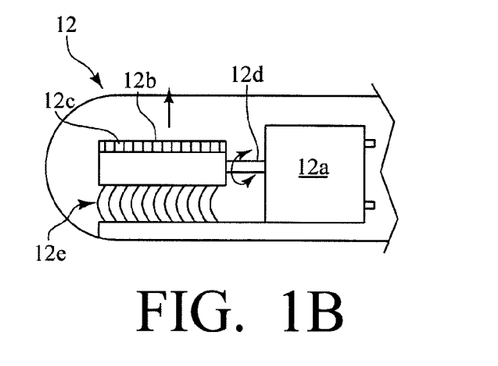
Figure 1C:
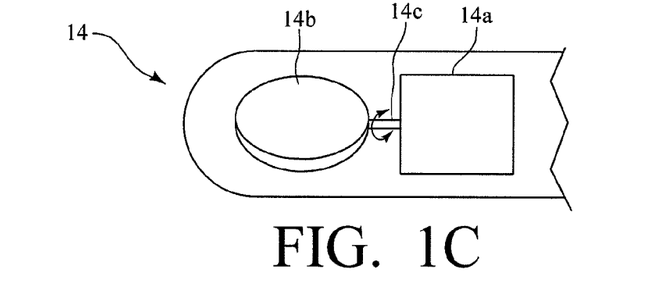

Before considering the preferred embodiments of the present invention, reference is made to FIGS. 1(a), 1(b) and 1(c), which show various approaches or modes for providing rotational movement of a transducer in an ultrasonic scanhead, all of which use either a remotely located motor or a motor directly coupled to the transducer to be rotated.

Referring to FIG. 1(a), there is shown a schematic cross-sectional first prior art probe 10 including a probe body 10a containing a motor-driven drive gear 10b that drives an intermediate gear 10c that, in turn, drives ring gear 10d mounted on a rotatable transducer unit 10e so as to extend around the circumference thereof. Transducer unit 10e is of conventional construction including a transducer array 10f and is mounted such that the longitudinal axis 10g thereof extends orthogonal to the longitudinal axis of the probe 10. The drive mechanism including gears 10b, 10c and 10d converts rotation of drive gear 10b into rotation of transducer unit 10e around its longitudinal axis 10g.

In the prior art probe 12 of FIG. 1(b), a motor 12a drives a transducer unit 12b including a transducer array 12c and mounted on a motor-driven driveshaft 12d. The requisite electrical connections to transducer unit 12b are indicated at 12e.

Referring to FIG. 1(c), there is shown a prior art probe device 14 including a motor 14a which drives transducer unit 14b of a disc-shape configuration through an intermediate driveshaft 14c.

Figure 2:
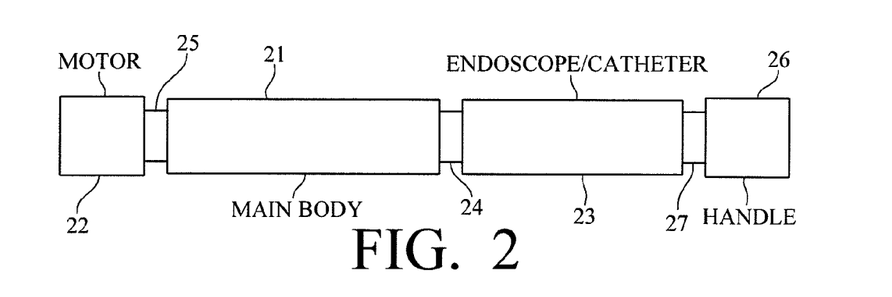
FIG. 2 is a block diagram of the basic elements of a scanhead assembly in accordance with the invention.

A scanhead in accordance with the present invention will now be described in connection with FIG. 2 where a scanhead main body 21 is connected at its proximal end (on the right side as viewed in FIG. 2) to a tubular endoscope/catheter 23 via an interconnect system 24 that can comprise a suitable mechanical connection (e.g., a rod- or thread-like connector) or a suitable adhesive or glue. At the distal end (the left side as viewed in FIG. 2), the scanhead main body 21 is attached to a motorization unit or motor 22 by connection means 25 which can again comprise a suitable mechanical connection or an adhesive. An important feature of the scanhead of FIG. 2 is that motorization unit 22 is located at the distal end of the scanhead apparatus as illustrated. The tubular body 23 is also connected to an endoscope/catheter handle 26 by connection means 27 which include seals for preventing liquid infiltration. It will be understood that the block diagram of FIG. 1 is intended to illustrate a basic feature of the invention and should not be interpreted as limiting the invention in any way. For example, a scanhead, main body 21 can also be of a shape other than the cylindrical shape illustrated.

It will also be understood by those skilled in the art that while important objects of the present invention concern an ultrasonic scanhead for endoscope/catheter use, endoscope/catheter devices are well known per se and no specific description of such endoscope/catheter devices is provided here. In general, any kind of endoscope/catheter device can be used in achieving the objects of the present invention.

Figure 3:
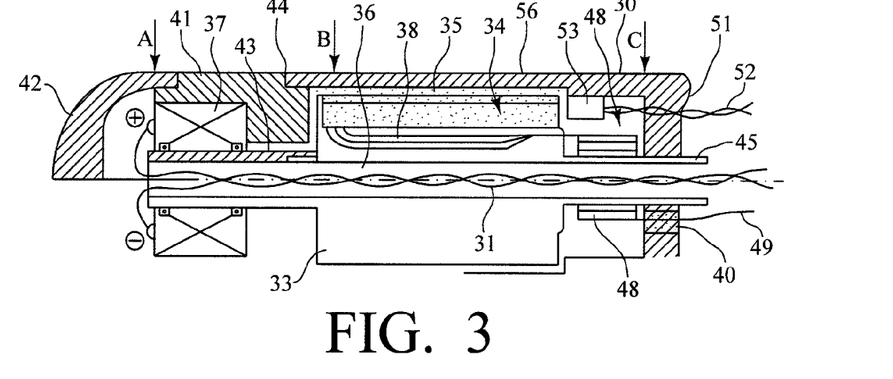
FIG. 3 is a longitudinal cross section of one preferred embodiment of the ultrasonic scanhead of the invention.

Referring to FIG. 3 there is shown the internal construction of an ultrasonic scanhead in accordance with a first preferred embodiment. An array transducer 34 that may be of a type having linear or phased arrays is connected to a longitudinally extending flexible interconnection circuit 38 that extends externally from a transducer carrier or mounting member 33.

The transducer carrier 33 preferably comprises a molding for one or more array transducers 34 which is made from a resin or resins such as epoxies or polyurethanes. The molding formed by carrier 33 comprises a cylindrical portion having a first diameter which matches the internal diameter of a scanhead housing 30 with a small clearance for receiving a coupling grease or liquid 35. A second diameter portion is provided on the right side of the carrier 33 as viewed in FIG. 3 which is of a smaller diameter than the first diameter and serves to provide guidance in positioning the carrier 33 into the housing 30. A third diameter portion is provided on the left side of the carrier 33 as viewed in FIG. 3 and is adapted to be coupled to the armature or driveshaft of motorization means or motor 37 so as to provide rotation of the carrier 33. A hollow bore or through space 36 is also provided in carrier 33 which extends coaxially with respect to the axis of symmetry of the scanhead which provides a passageway for electrical wires 31 of the motor power supply.

The housing 30 is preferably made of an acoustically transparent material or materials such as TPX™, polysulfone or a high density polyethylene (PE) so as to provide smooth transmission of ultrasonic energy and to avoid reflections of this ultrasonic energy from the material itself.

In an alternative construction housing 30 can be made from any rigid material (e.g., a polymer or metal can be used in making the housing body) but with the inclusion of a cylindrical acoustically transparent window (not shown) in alignment with the transmitting surface of array transducer 34 during scanning of transducer 34 so that the ultrasonic energy passes through this window.

Since the electrical wires 31 for energizing motor 37 are placed along the central longitudinal axis of carrier 33, wires 31 will, therefore, remain static, i.e., do not move. During a scanning operation, the array transducer 34 can be rotated through an angle of 360 degrees, or more, if desired. The motorization means or motor 37 can, for example, be a motor selected from the group consisting of DC, synchronous and stepping motors, is, as shown, mounted axially with respect to the transducer carrier 33 and housing 30.

Preferably, motor 37 is equipped with a hollow shaft 43 that is secured to a third diameter portion of carrier 33 as shown in FIG. 3 in a manner so as to form an internal passageway for the electrical cables of the motor 37. Motor 37 is precisely mounted in a support member 41 which, in turn, fits into and, in essence, forms part of the housing 30 through means of a shoulder 34 that provides sealing and guidance in positioning of the overall motor assembly. It is noted that, as illustrated, support member 41 and housing 30 have the same external diameter after assembly. When assembled together, motor 37, support member 41 and housing 30 are then secured together by an adhesive (e.g., a glue) or by mechanical means.

The scanhead device as so assembled is then terminated at the distal end by a cap 42 made of a material of the same type as that of support member 41, and which will seal the housing by its distal tip.

At the proximal end of the ultrasonic array transducer, an interconnection volume or area 48 is defined or delimited by the transducer carrier 33, an elongated shaft or axle 45 and the internal cavity of housing 30. In volume 38 there is disposed an interconnection means 48 which, in a preferred embodiment, comprises flexible circuits coiled around shaft or axle 45 so as to permit the rotation of the transducer 34 without any torsional effect on the flexible circuits comprising interconnection means 48. The number of turns around shaft or axle 45 necessary to prevent this torsional effect depends on the maximum amplitude of the rotation of transducer 34 and the velocity at which the transducer 34 is to be rotated. Typically, three to five turns of the flexible circuit 48 are sufficient to enable most scanning operations to be carried out. The flexible circuits 48 are secured at one end to the transducer carrier 33 and at the other end to an opening 40 in housing 30. Opening 40 is sealed, e.g., by a silicon rubber or an adhesive (glue). Once the sealing operation is complete, an external portion 49 of the flexible circuit 48 will consequently be isolated from any movement and/or vibration of the coiled portion of the flexible circuits 48.

Further, the area or volume 38 preferably contains an incremental encoding device 53 which is used to detect rotation and rotational speed information with respect to the transducer carrier 33 through use of a conventional encoding disk (not shown) affixed to the proximal end of the carrier 33.

Electrical wires 52 for the encoding device 43 pass through housing 30 and are sealed at the exit point 51, with, e.g., a flexible glue (such as silicon rubber or the like).

Acoustic coupling between the transducer 34 and housing 30 is provided by the aforementioned coupling liquid or grease 35 which is preferably of a uniform thickness. Coupling liquid 35 is disposed on thin "window" portion 56 of housing 30. A space is provided between the surface of transducer 34 and the internal surface of window portion 56 is such as to provide the assembly with capillarity forces that are sufficiently high to maintain the coupling liquid 35 in place during operation. Typically, these surfaces are separated by a distance ranging from 0.1 mm to 0.5 mm. Preferably, the opposing surfaces of housing 30 and transducer 34 that define or delimit the acoustic coupling zone are coated with low surface tension force material or plasma of a nature such as to improve the capillarity effect. Liquids that are well suited for coupling the acoustic energy in biologic tissue include water, paraffin oil, propandiol glycol and the like. Coupling greases or liquids that can be selected for use include silicon types, and these can be mixed with mineral particles so as to increase the frictional properties and acoustic impedance.

Figure 4:
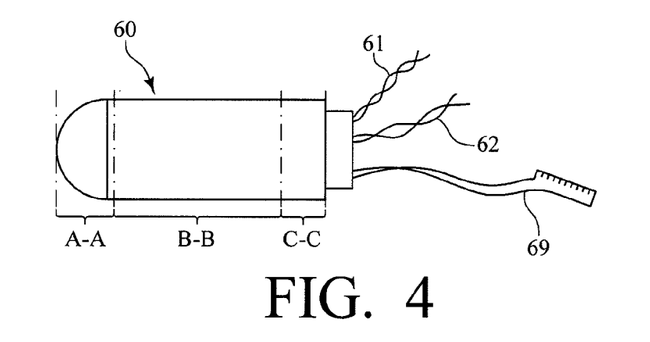
FIG. 4 is a side elevational view of a scanhead showing external features thereof.

Referring to FIG. 4, there is shown a scanhead or probe device in accordance with a preferred embodiment of the invention. The external construction of the scanhead device is illustrated. In FIG. 4 the device, which is generally denoted 60, includes a portion A-A which is located at the distal or outermost end of the device and in which the motorization means (not shown) is housed. Distal portion A-A is located adjacent to an intermediate portion B-B in which the ultrasonic transducer (not shown) is located and which is provided with an acoustically transparent window (not shown) for the passage of energizing ultrasonic waves. A proximal portion C-C serves as a junction between the scanhead and the endoscope/catheter device. Portion C-C is an extension of the portion B-B and forms part of the tubular portion of the scanhead device. Portion C-C serves as a receptacle for an interconnection means (not shown) and a position encoder (not shown). Finally, wires 61, 62 and a flexible circuit 69 extend from the proximal end of the scanhead to the handle of the probe where they are connected to external cables (not shown).

Figure 5A:
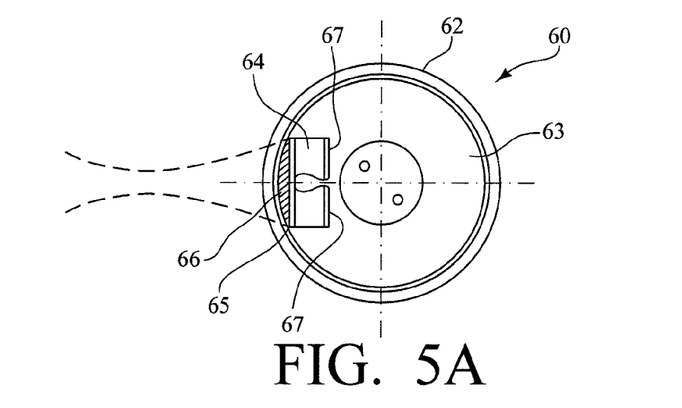
FIG. 5(a) is a transverse cross-sectional view of one preferred embodiment of the invention incorporating a single array transducer.

Referring to FIG. 5(*a*), there is shown a transverse cross-sectional view of one embodiment of the scanhead of the probe device 60 of FIG. 4. In FIG. 5(*a*), transducer carrier 63 is mounted for rotation inside of housing 62 and carries a single array transducer 64 including transducer elements 65 and a focusing lens 66. Electrical connections to transducer elements 65 are indicated at 67.

Figure 5B:
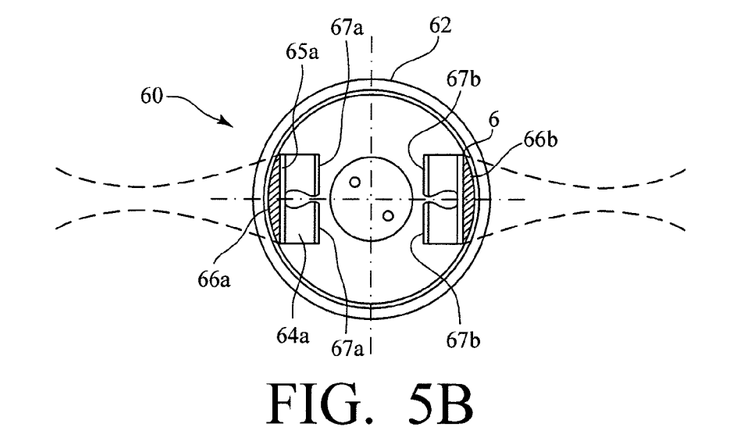
FIG. 5(b) is a transverse cross-sectional view of a further preferred embodiment of the invention incorporating a pair of array transducers mounted in an opposed relation.

FIG. 5(*b*) is similar to FIG. 5(*a*) except that two oppositely disposed array transducers 64*a* and 64*b* are employed. The other parts common to the two array transducers are similar and are given the same reference numerals with an "a" attached for array transducer 64*a* and with a "b" attached for array transducer 64*b*. In a preferred embodiment, the transducer elements 65*a* are of a first configuration and transducer elements 65*b* are of a second, different configuration, and array transducer 64*a* is of a first resonant frequency and array transducer 64*b* is of a second, different resonant frequency.

Figure 6:
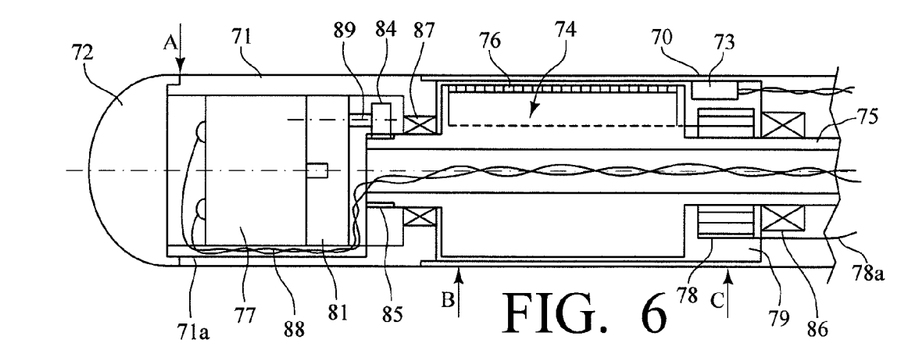
FIG. 6 is a longitudinal cross section of a scanhead in accordance with a further embodiment of the invention.

FIG. 6 illustrates an advantageous variant of the preferred embodiment wherein a conventional motorization means is mounted so as to provide rotation of a proximally located transducer. The scanhead of FIG. 5 comprises housing 70 having portions of first and second internal diameters for receiving a transducer 74. The latter is guided by its proximal shaft 75 into the housing 70. Transducer 74 is actually molded into a cylindrical shape so as to fit internally within the larger diameter portion of housing 70. The space remaining between the transducer 74 and the housing 70 is then filled by coupling liquid or grease 76 for promoting good propagation of acoustic energy.

A position encoder 73 is mounted in the vicinity of the transducer 74 to provide the remote imaging system with accurate information with respect to the position and speed of the transducer 74.

An output interconnection means 78 for transducer 74 comprises flexible circuits coiled around the transducer shaft 75. The interconnection means (flexible circuits) 78 is secured at one end to the transducer mounting portion of housing 70 (not shown) while the other end passes through housing 70 and extends outwardly thereof at 78*a* to enable connection to external cables (not shown).

Encoder 73 and interconnection means 78 are housed in a space 79 formed by the major diameter portion of the housing 70 and the transducer support portion. In order to provide additional guidance during the assembly of the housing/transducer, a bearing 86 is disposed at the entrance of the smaller diameter portion of the housing 70.

The transducer support terminates at the distal end at a reduced diameter portion having mounted thereof at its extremity, a gear 85 which engages a corresponding gear 84 on a motor output gear shaft 89. In the embodiment illustrated, motorization means 77 is optionally provided with gear reduction gearbox 81 including the output shaft 89 terminated by gear 74. Gearbox 81 is secured to a support member 71 which is, in turn, affixed to housing 70 so as to form an elongate scanning device including a forwardly or distally located motorization means 77. It is noted that a proximal portion of support member 71 can be provided with a bearing 76 to provide smoother rotation of the transducer unit 74.

The gearing system comprising gears 84 and 85 can be made of plastic so as to reduce operating noise and/or avoid the need for a lubricant such as usually recommended for metal parts. Because the motor shaft 89 is not of a hollow shape as shown in FIG. 3, a groove 71*a* in the internal diameter of support member 71 provides a passageway for the electrical power supply wires 88 for the motor 77. Preferably, the position of the motor 77 with respect to support member 71 is such that gears 84 and 85 mate perfectly once the support member 71 is properly assembled with respect to housing 70. It will be appreciated that with the arrangement just described, the assembly operation is simplified during manufacturing and the maintenance needed is also reduced.

A cap 72 is located at the distal end of the scanhead device and covers the distal opening of support member 71 so as to protect the motor 77 and provides smooth terminating shape to the end tip of the device.

In order to make the scanhead compatible with medical uses, the materials used for housing 70, support member 71 and cap 72 are preferably selected from medical grade plastics such as PEBAX™, TPX™, PEEK™, ULTEM™ and the like. An EMI coating can also advantageously be provided on the internal surface of cap 72 and on support member 71. This coating is connected to the electrical ground of the imaging system to improve the signal to noise ratio. Similarly, housing 70 may be EMI protected as well. However, care must be taken to avoid an excessive coating thickness in the region of housing 70 at which acoustic waves are transmitted. In this regard, the coating thickness in this region preferably should not exceed a half of a micron. Suitable materials for EMI coating in the region of the acoustic window include copper and gold. The use of an adhesion precursor will further improve the durability of the coating. Shielding products and processes that can be used include coating systems such as Unishield® from Unitech, SuperShield conductive coating from MG Chemicals, and vaporization techniques such as chemical vapor deposition (CVD) including APCVD (atmospheric pressure chemical vapor deposition), LPCVD (low pressure CVD), PACVD (plasma assisted CVD), PECVD (plasma enhanced CVDDV), PCVD (photo CVD), LCVD (laser CVD), MOCVD (metal-organic CVD), CBE (chemical beam epitaxy), CVI (chemical vapor infiltration) and physical vapor deposition (PVD) including sputtering, MBE (molecular beam epitaxy) and thin film growth techniques such as spray coating, electroplating and liquid phase epitaxy.

Figure 7A:
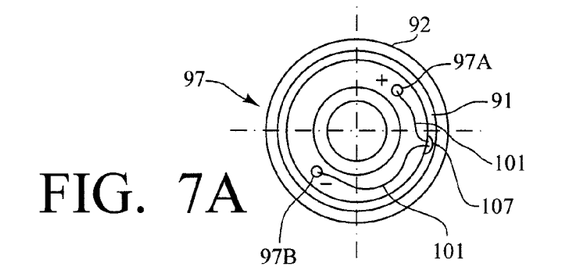
FIG. 7(a) is a transverse cross-sectional view taken generally along line A-A of FIG. 2.
Figure 7B:
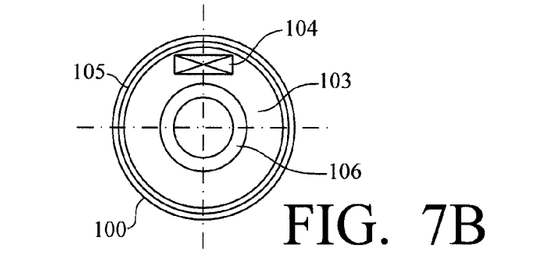
FIG. 7(b) is a transverse cross-sectional view taken generally along line B-B in FIG. 2.
Figure 7C:
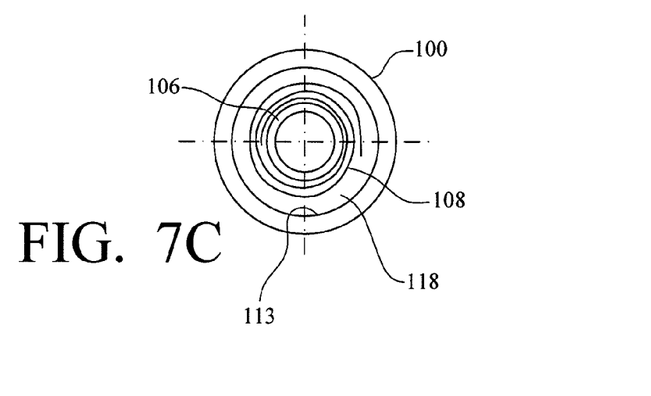
FIG. 7(c) is a transverse cross-sectional view taken generally along line C-C in FIG. 2.

FIGS. 7(a) to 7(c) illustrate three different cross-sectional views, A, B and C, of a scanhead generally depicted as in FIG. 3 and FIG. 6 which by arrows A, B and C show the locations at which the sections A, B and C are taken. In the view corresponding to section A shown in FIG. 7(a), a motor 97 is viewed from the rear side thereof, and interconnection pads 97a and 97b are provided for powering the motor 97 are also illustrated. A support 91 and cap 92 show the manner in which the motor 97 is mounted. A groove 107 is shown in cross section view and includes motor wires 101 adapted to be connected to the motor pads 97a, 97b.

As shown in FIG. 7(a), the motor portion of the scanhead can be assembled and disassembled from the scanhead housing simply by first disconnecting motor wires 97a and 97b. Then support member 91 can be safely removed from the housing without any risk of damage to the scanhead. The reverse operation can be carried out by assembling the support member 91 first and then by soldering the wires 97a and 97b to the motor 97. This mechanical construction of the scanhead is highly advantageous when applied to surgical ultrasonic devices requiring maintenance operations.

In embodiments wherein the motor 97 is provided with a hollow shaft through which the wires 97a, 97b extend, groove 107 is not needed and wires extending from the center of the motor 97 are connected motor pads 97a and 97b.

Section B, located on the proximal side of section A, is shown in FIG. 7(b) and is a sectional view of a transducer 104 and a transducer carrier 103. Modifications and variations that can be applied to this section have been described in FIGS. 5(a) and 5(b), and the transducer 104 shown in FIG. 7(b) is shown as being embedded in the carrier 103. Carrier 103 includes a hollow space 106 through which pass the electrical wires for motorization means for the scanhead. Transducer 104 is positioned at the periphery of carrier 103 in such as manner as to contact a coupling medium 105 which acoustically couples ultrasonic energy between the transducer 104 and a housing 100, through an acoustic window (not shown in FIG. 7(b)).

It will be understood that while FIG. 7(b) only shows a single transducer 104 for purposes of simplicity of illustration, a plurality of independent transducers corresponding to transducer 104 can be provided in positions around the periphery of the carrier 103.

Referring to FIG. 7(c), section C is shown which is taken further along the proximal side of the scanhead. FIG. 7(c) shows, in section, housing 100, an interconnection flex circuit 108, a hollow shaft 106 and a space 118 which houses the above described interconnection means (flex circuit) 108 and a position encoder device 113. In the latter regard, on the bottom side of space 118 there is illustrated schematically the position encoder 113 which is mounted in front of the abovementioned incremental disk (not shown in FIG. 7(c)) preferably attached to the transducer carrier 103.

Figure 8:
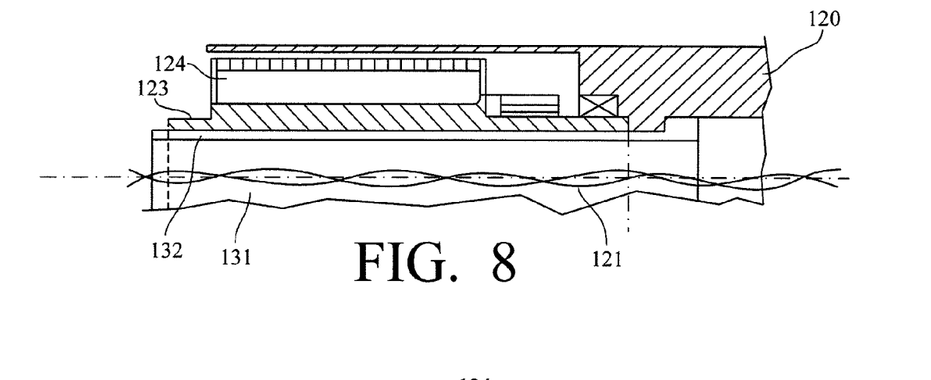
FIG. 8 is a cross-sectional view of a scanhead in accordance with yet another embodiment of the invention.

Still another improvement that can be implemented in the scanhead of the previously described preferred embodiments of FIG. 3 and FIG. 6, is shown in FIG. 8. FIG. 8 is a simplified functional view of a scanhead comprising a housing 120 corresponding to that described, a transducer 124 and a carrier 123. So as to avoid any wearing contact between the wires 121 which pass through the carrier 123 and the internal cylindrical surface of the carrier 123, a cannula 132 made from a low friction coefficient material is provided in the hollow space 131 defined by carrier 123. Cannula 132 is secured to housing 120 so as to remain fixed during the rotation of the transducer 124 and its carrier 123. A scanhead device equipped with the cannula 132 has the advantage of preventing wearing of wires 121 located therein and, therefore, of increasing the reliability and the lifetime of the scanhead. The scanhead construction of FIG. 8 is otherwise similar to those described above and thus will not be described further.

Figure 9A:
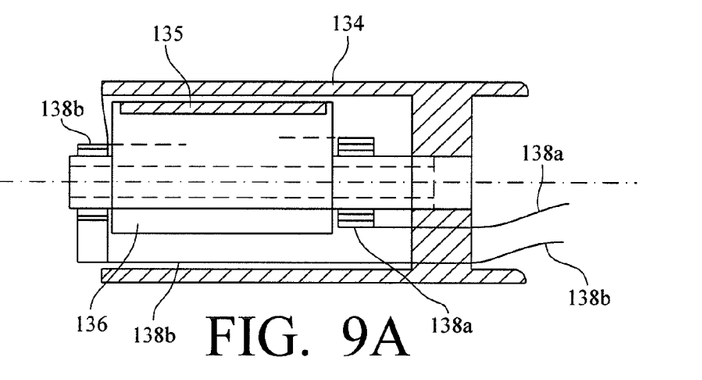
FIG. 9(a) is a longitudinal cross-sectional view of a scanhead in accordance with a further embodiment of the invention, and incorporating a dual flex output.
Figure 9B:
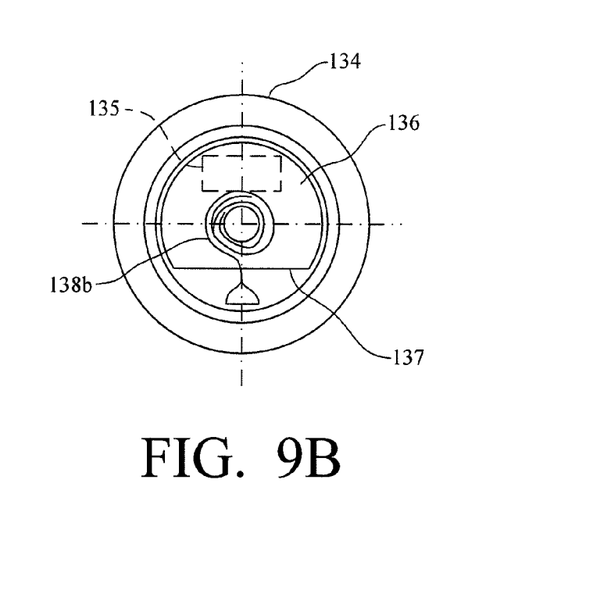

Referring to FIGS. 9(a) and 9(b), there is shown a modification of the abovedescribed preferred embodiments wherein the flexible interconnection circuits or flex circuits are provided on both sides of the transducer carrier. This configuration of the flex circuits is particularly suitable for either a very high density array transducer where the use of dual output flex circuits is mandatory or for a scanhead construction wherein the transducer is to be rotated through an angle less than or equal to 90 degrees. It will be understood that all other features of the preferred embodiments described above are applicable to this embodiments as well.

In the embodiment of FIGS. 9(a) and 9(b) a housing 134 including a transducer 135 and its carrier 136 are similarly mounted together as described in connection with previous embodiments. Flex circuits 138a and 138b are located on both sides of the transducer carrier 136 and are coiled around in smaller diameter coils are shown by FIGS. 9(a) and 9(b). Because the flex circuit 138a is managed or handled as previously described above in connection with FIGS. 3 and 6, flex circuit 138b extends from the distal side of carrier 136 and then coiled around the shaft of the carrier 136 and is folded in such a manner as to extend to the region of flex circuit 138a and from there to pass through the housing 134.

In order to enable the transducer carrier 136 to be rotated without an interference from flex circuit 138b, carrier 136 is of a truncated diameter and includes a flat portion 137 shown in FIG. 9(b) so as to provide room for circuit mounting. It is important to note that the flat portion 137 of carrier 136 may be defined according to the amount of rotation of the transducer 135 so that portion 137 can be of a flat shape or a V shape or a curved shape or the like.

In order to prevent problems associated with the capillarity of the coupling liquid, the distance between the transducer/carrier surface and surface defining the internal diameter of the housing 134 should be carefully selected based on the viscosity of the coupling liquid or grease employed.

Figure 10:
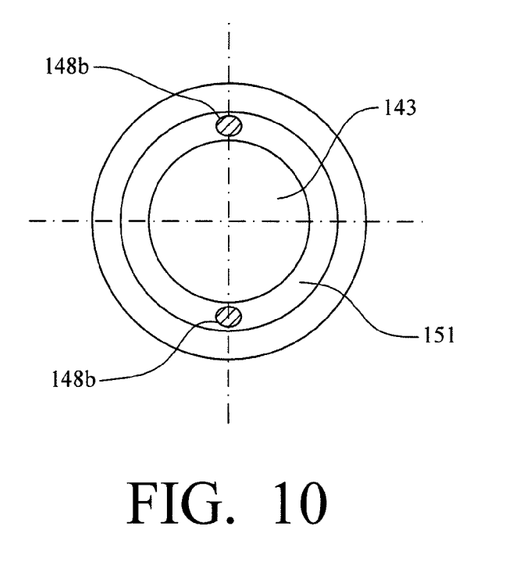
FIG. 10 is a transverse cross section of a cannula showing embedded electrical wires for motor connections.
Figure 11:
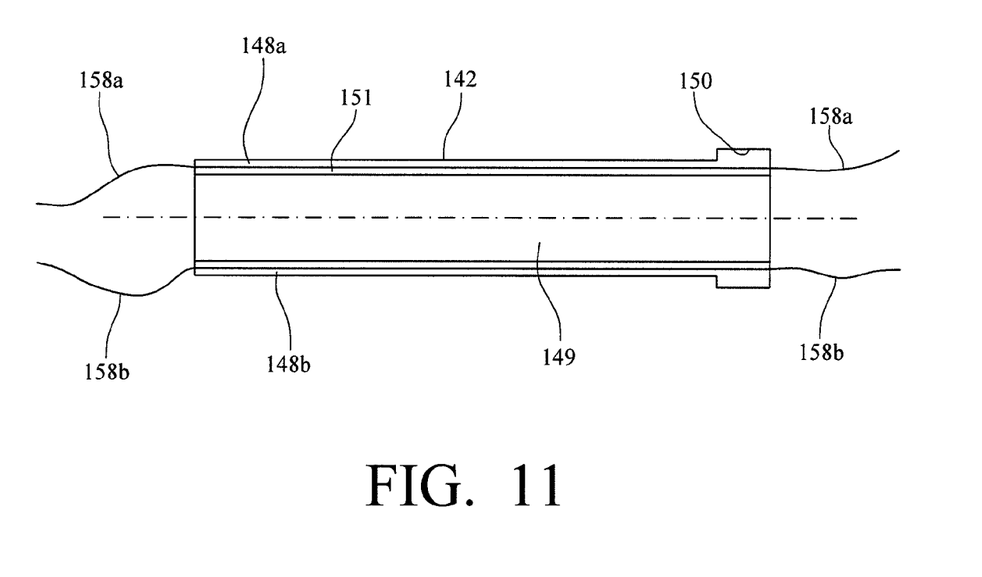
FIG. 11 is a longitudinal cross-sectional view of the cannula of FIG. 10.

FIGS. 10 and 11 show a further improvement of the scanhead apparatus where a central cannula is designed so as to integrate the electrically conductive wires in its wall thickness, and thus provide the electrical connection for the motor without any wires passing through the hollow space defined within the scanhead apparatus. This space or passage can, therefore, be dedicated to insertion of other surgical instruments for diagnostics, biopsy or treatment. It will be apparent to those of ordinary skill in the art that when such a passage is provided for the insertion of instruments, insertion can be made through the endoscope/catheter probe in a manner so as to enable external access for these instruments (end-finger or lateral openings are compatible).

Referring specifically to the embodiment illustrated in FIGS. 10 and 11, a cannula 142 as shown in FIGS. 10 and 11 is provided with a shoulder portion 150 that acts as mechanical abutment for mounting the cannula 142. A cylindrical portion 151 that extends along the transducer carrier 143 includes, in the thickness thereof, embedded conductive wires or traces 148a and 148b. The latter are externally connected to conductive wires 158a and 158b which may simply be external extensions thereof as indicated by the curved portions that extend beyond the cannula 142 on both sides thereof. A hollow space 149 is provided which has dimensions that are determined to be compatible with standard working channel diameters so as to permit the insertion of surgical instruments therein.

The use of the cannula 142 illustrated in FIGS. 10 and 11 enables mounting of a hollow shaft motor type for instrument insertion, as shown in FIG. 3. Cannula 142 is preferably made from plastic or composite materials that exhibit non-electrically conductive properties, i.e., insulating materials, so as to provide electrical isolation of the wires or traces 148a and 148b.

Although the invention has been described above in relation to preferred embodiments thereof, it will be understood by those skilled in the art that variations and modifications can be effected in these preferred embodiments without departing from the scope and spirit of the invention.

What is claimed:

1. An ultrasonic scanhead which is configured for assembly onto a scanning probe and which enables scanning of a cylindrical volume, said scanhead having a major longitudinal axis and said scanhead comprising:
    (a) a transducer portion including mounted thereon at least one linear array transducer longitudinally aligned with the major longitudinal axis of the scanhead;
    (b) a removable motorization portion mounted at a distal end of the transducer portion so as to be removable without disassembly of the scanhead from a scanning probe onto which the scanhead is assembled, said motorization portion including motorization means for providing rotation of said at least one linear array transducer about an axis in alignment with said major longitudinal axis;
    (c) a proximal portion configured to be connected to or plugged into the scanning probe, said proximal portion including transducer interconnection means for connection to the at least one linear array transducer and a position encoder for detecting the rotational position of the at least one linear array transducer; and
    (d) said scanhead further including a central hollow space coaxially aligned with the major longitudinal axis of the scanhead and extending from the proximal portion through the transducer portion to the motorization portion, said space housing electrical interconnections for the motorization means.

2. An ultrasonic scanhead according to claim 1 wherein the scanhead includes a housing defining an internal diameter, and the transducer portion comprises a transducer unit of a cylindrical shape configured to fit within the internal diameter of the scanhead housing.

3. An ultrasonic scanhead according to claim 2 wherein a coupling material is disposed between the scanhead housing and the transducer unit and is maintained in place by capillary force.

4. An ultrasonic scanhead according to claim 3 wherein opposed surfaces of scanhead housing and transducer unit are separated by a distance that results in the capillary forces necessary to maintain the coupling material in place.

5. An ultrasonic scanhead according to claim 3 wherein the coupling material comprises one of liquids and greases.

6. An ultrasonic scanhead according to claim 1 wherein the interconnection means for the at least one linear array transducer comprises flexible circuits extending from a flat surface of the transducer unit and wherein said flexible circuits are coiled around a support element coaxial with the longitudinal axis of said transducer unit so as to allow the transducer unit to rotate without wearing contact being exerted on the flexible circuits.

7. An ultrasonic scanhead according to claim 1 wherein the motorization means of said motorization portion comprises a distally mounted motor including a hollow central shaft providing a passageway for electrical wiring for said motor.

8. An ultrasonic scanhead according to claim 1 wherein the motorization portion comprises a wall portion having grooves therein for receiving motor wiring.

9. An ultrasonic scanhead according to claim 1 wherein said at least one array transducer comprises first and second linear array transducers and wherein said first and second linear array transducers are arranged linearly with respect to one to the other in a head to tail configuration.

10. An ultrasonic scanhead according to claim 1 wherein said at least one linear array transducer comprises first and second linear array transducers and wherein said first and second linear array transducers are disposed in a diametrically opposed relation.

11. An ultrasonic scanhead according to claim 1 wherein the at least one linear array transducer comprises at least one phased array transducer.

12. An ultrasonic scanhead according to claim 1 wherein the at least one linear array transducer comprises at least one 1.5D array transducer.

13. An ultrasonic scanhead which is configured for assembly onto a scanning probe and which enables scanning of a cylindrical volume, said scanhead having a major longitudinal axis and said scanhead and comprising:
    (a) a transducer portion including a transducer assembly comprising at least one linear array transducer longitudinally aligned with the major axis of the scanhead, transducer interconnection means for the at least one linear array transducer provided at both the distal and proximal ends of the at least one linear array transducer, and a space disposed outwardly of the transducer assembly with respect to the major longitudinal axis of the scanhead in such a manner to provide a passageway for a part of the distal transducer interconnection means and for a part of a motorization interconnection means so that each of said parts extends to the location of the proximal transducer interconnection means;
    (b) a removable motorization portion, connected to said motorization interconnection means, mounted at a distal end of the transducer portion and configured to be removed without disassembly of the scanhead from the scanning probe, said motorization portion including motorization means for providing rotation of said at least one linear array transducer about an axis in alignment with said major longitudinal axis; and
    (c) a proximal portion configured to be connected to or plugged into a body portion of the scanning probe body and including a part of said transducer interconnection means and a position encoder for said transducer assembly.

14. An ultrasonic scanhead, configured for assembly onto a scanning probe, for enabling scanning of a cylindrical volume, said scanhead having a major longitudinal axis and comprising:

(a) a transducer portion including at least one linear array transducer aligned longitudinally with respect to the major longitudinal axis of the scanhead;
(b) a removable motorization portion mounted at the distal end of the transducer portion and configured to be removed without disassembly of the scanhead from an associated scanning probe, said motorization portion including motorization means for providing rotation of said at least one linear array transducer about an axis in alignment with said major longitudinal axis;
(c) a proximal portion configured to be connected to or plugged into a probe body of the associated scanning probe and including transducer interconnection means; and
(d) a central hollow space coaxially aligned with the major longitudinal axis of the scanhead and extending from the proximal portion through the transducer portion and the motorization portion so as to open to the outside and to thus enable passage therethrough of a surgical or diagnostic instrument.

15. An ultrasonic scanhead for assembly onto a scanning probe for enabling rotation of an associated transducer unit, said scanhead having a major longitudinal axis and comprising:

(a) a transducer portion including mounted therein, at least two linear array transducers disposed oppositely one to the other and aligned longitudinally with the major longitudinal axis of the scanhead, the first array transducer having a first resonant frequency and a first transducer element configuration; and the second array transducer being mounted oppositely to the first array transducer with respect to the longitudinal axis of the scanhead and having a second resonant frequency and a second transducer element configuration;
(b) a removable motorization portion mounted at the distal end of the transducer portion and configured to be removed without disassembly of the scanhead from an associated scanning probe, said motorization portion including motorization means for providing rotation of said at least one linear array transducer about an axis in alignment with said major longitudinal axis;
(c) a proximal portion configured to be connected to or plugged into a probe body of the associated scanning probe, said proximal portion including transducer interconnection means and position encoding means; and
(d) a central hollow space coaxially aligned with the major longitudinal axis of the scanhead and extending from the proximal portion through the transducer portion to the motorization portion so as to enable electrical interconnections to be made to the motorization means.

* * * * *